(12) United States Patent
Lo Priore

(10) Patent No.: US 12,050,178 B2
(45) Date of Patent: Jul. 30, 2024

(54) DETECTOR FOR MEASURING FLUORESCENCE IN A LIQUID SAMPLE

(71) Applicant: HYRIS LIMITED, London (GB)

(72) Inventor: Stefano Lo Priore, Lugano (CH)

(73) Assignee: HYRIS LIMITED, London (GB)

( * ) Notice: Subject to any disclaimer, the term of this patent is extended or adjusted under 35 U.S.C. 154(b) by 0 days.

(21) Appl. No.: 18/090,563

(22) Filed: Dec. 29, 2022

(65) Prior Publication Data

US 2023/0144851 A1 May 11, 2023

Related U.S. Application Data

(63) Continuation of application No. 15/545,063, filed as application No. PCT/IB2016/050226 on Jan. 18, 2016, now abandoned.

(30) Foreign Application Priority Data

Jan. 20, 2015 (IT) .......................... RM2015A000027

(51) Int. Cl.
*G01N 21/64* (2006.01)
*B01L 99/00* (2010.01)
(Continued)

(52) U.S. Cl.
CPC ......... *G01N 21/6428* (2013.01); *C12Q 1/686* (2013.01); *G01N 21/645* (2013.01); *G01N 21/6452* (2013.01); *G01N 21/6456* (2013.01); *G01N 27/07* (2013.01); *G01N 2021/6439* (2013.01); *G01N 2021/6463* (2013.01);
(Continued)

(58) Field of Classification Search
CPC ........... C12Q 1/686; G01N 2021/6439; G01N 2021/6463; G01N 2021/6471; G01N 2021/6478; G01N 2021/6482; G01N 21/6428; G01N 21/645; G01N 21/6452; G01N 21/6456; G01N 27/07
See application file for complete search history.

(56) References Cited

U.S. PATENT DOCUMENTS

2003/0222223 A1* 12/2003 Kamei ................ G01N 21/255
250/216
2006/0078929 A1 4/2006 Bickel et al.
(Continued)

FOREIGN PATENT DOCUMENTS

| WO | 2012151358 | 11/2012 |
| WO | 2014020977 | 2/2014 |
| WO | 2014210593 | 12/2014 |

OTHER PUBLICATIONS

International Search Report and Written Opinion for International Patent Application PCT/IB2016/050226 mailed Apr. 22, 2016.

*Primary Examiner* — Lydia Edwards
(74) *Attorney, Agent, or Firm* — ArentFox Schiff LLP

(57) ABSTRACT

The present invention relates to a detector for measuring fluorescence in a liquid sample and to devices for biochemical analyses comprising it, in particular to devices for performing analyses of real time PCR. The detector of the present invention has a series of advantages such as drastic simplification of the detection configuration, reduced costs, better performances due to the greater freedom in planning the optical configuration which allows dividing the detector itself into independent areas.

20 Claims, 7 Drawing Sheets

(51) Int. Cl.
  *C12Q 1/686* (2018.01)
  *G01N 27/07* (2006.01)
(52) U.S. Cl.
  CPC .............. *G01N 2021/6471* (2013.01); *G01N 2021/6478* (2013.01); *G01N 2021/6482* (2013.01)

(56) References Cited

U.S. PATENT DOCUMENTS

| | | |
|---|---|---|
| 2010/0311070 A1 | 12/2010 | Oh et al. |
| 2013/0288259 A1* | 10/2013 | Tajima .................. G01N 35/04 |
| | | 435/6.12 |
| 2014/0203173 A1 | 7/2014 | Krufka |
| 2015/0177150 A1 | 6/2015 | Rothberg et al. |
| 2015/0251184 A1 | 9/2015 | Watanabe et al. |

* cited by examiner

DETECTOR FOR MEASURING FLUORESCENCE IN A LIQUID SAMPLE

CROSS-REFERENCE TO RELATED APPLICATIONS

This application is a continuation of U.S. patent application Ser. No. 15/545,063, filed Jul. 20, 2017, which is a National Stage Entry of International Patent Application PCT/IB2016/050226, filed Jan. 18, 2016, which claims priority to Italian Patent Application No. RM2015A000027, filed Jan. 20, 2015, the disclosure of each of which are hereby incorporated by reference.

TECHNICAL FIELD OF THE INVENTION

The present invention relates to a detector for measuring fluorescence in a liquid sample and to devices for biochemical analyses including it, in particular to devices for performing analyses of real time PCR.

STATE OF ART

In the last years the spreading of molecular diagnostic tests based upon the amplification of nucleic acid sequences, and in particular the techniques using specifically planned fluorescent markers and enzymes, have allowed the quick and quantitative (or half-quantitative) analysis of nucleic acid sequences for a plurality of diagnostic applications, several thereof aimed at identifying pathogenic agents responsible for infective diseases, but even in other fields such as oncology and pharmacogenomics.

The most widespread technology is the Real-Time PCR (rtPCR), however a series of other methods, based upon both temperature cycles or isothermal reactions, is much used.

A great effort has been made to optimize the biochemical portion in this type of analysis, but the devices needed to perform the reactions and to acquire the results are still a factor limiting the spread of these analyses. In particular, the sizes, costs and skills required to use this type of instruments are still prohibitive.

In the state of art analysis systems are described wherein several detectors are used, each one dedicated to one specific detection wavelength. However, these devices have several disadvantages such as for example the lack in availability on the market of multi-sensor cameras, cost and complexity in producing a detector including several single detectors.

The patent application WO2012151358 describes a lighting apparatus comprising an array of light sources and a matrix of lenses coupled to a mechanical arm of the apparatus.

SUMMARY OF THE INVENTION

The technical problem placed and solved by the present invention is then to provide a detector allowing to obviate the drawbacks mentioned above with reference to the known art.

Such problem is solved by a detector according to claim 1 and by a device according to claim 9.

The present invention further provides the following advantages:

- a drastic simplification of the detection configuration, reduced costs, better performances due to the greater freedom in planning the optical configuration allowing to divide the detector itself into independent areas;
- optimizing the performances of the reactions, by improving at the same time the system reliability;
- improving considerably the instrument applicability by means of developing a design of the sample holder allowing the access to optics and electronics separated along different mechanical axes.

Preferred features of the present invention are subject of the depending claims.

Other advantages, features and use modes of the present invention will result evident from the following detailed description of some embodiments, shown by way of example and not for limitative purposes.

BRIEF DESCRIPTION OF THE FIGURES

The figures of the enclosed drawings will be referred to, wherein.

DETAILED DESCRIPTION OF PREFERRED EMBODIMENTS

Figure 1:
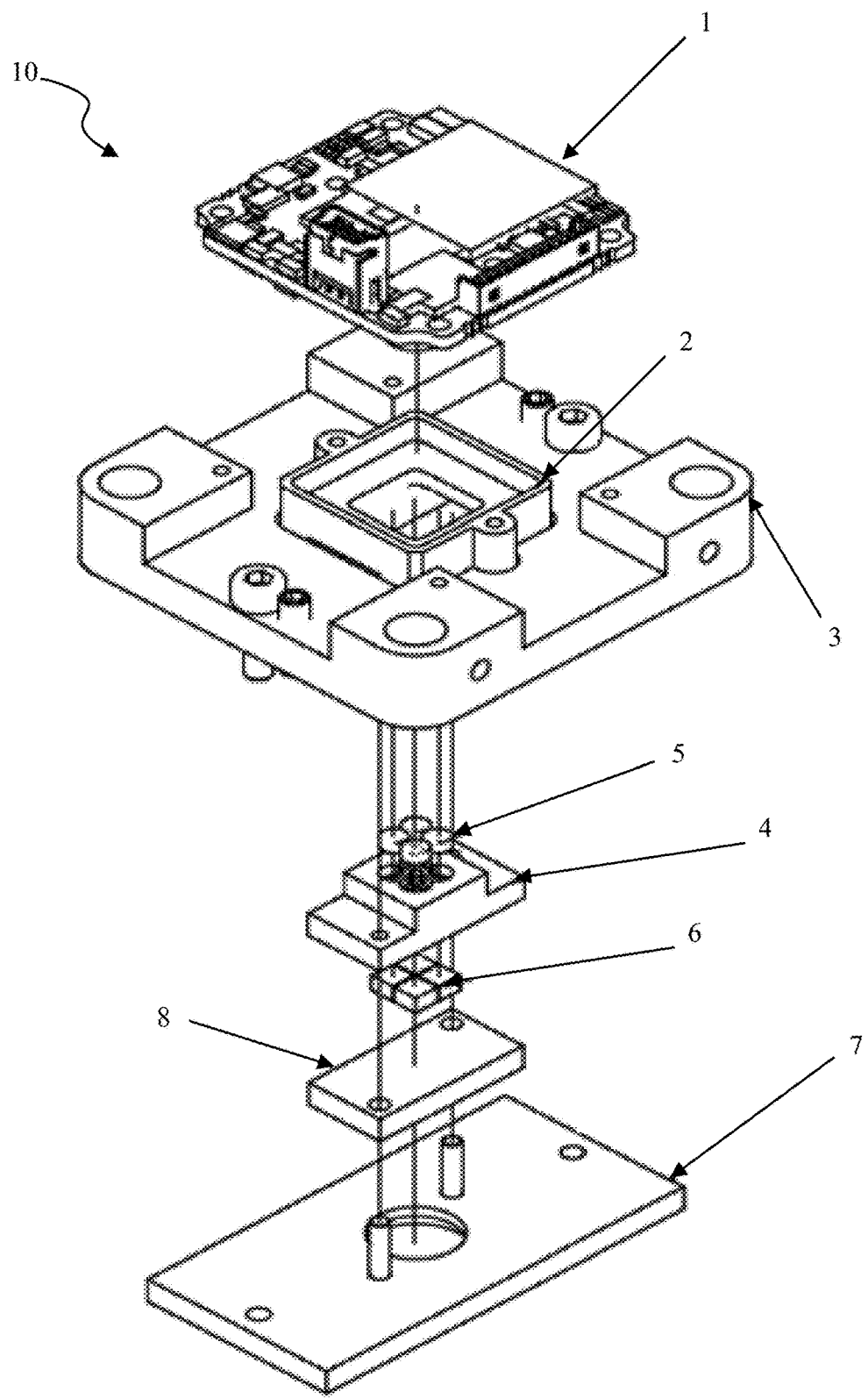
FIG. 1 shows an exploded view of a preferred embodiment of the detector according to the present invention.

By firstly referring to FIG. 1, a detector for measuring fluorescence in a liquid sample according to a preferred embodiment of the invention is designated as a whole with 10.

Inside the liquid sample which will be positioned in the suitable reaction area of the detector, not shown in figure, the chemical and biochemical reactions of interest will take place, which will be detected in qualitative or quantitative way according to the optically detectable reaction. In the embodiment of FIG. 1 the generated signal is of fluorescent type.

The detector 1, in the present example, comprises an optical sensor 1, particularly of the CMOS or CCD type, connected by suitable mechanical means 2, 3 to the optical unit.

The optical unit of the detector apart from comprising a light source for irradiating the liquid sample under examination comprises a plurality of optical filters 6 and of lenses 5, in the present example there are 4 different filters 6 and lenses 5, but according to other embodiments they could be 6, 8, 10, 20, etc. The filters could have different wavelengths according to the type of analysis which will be performed. According to an embodiment one or more of said lenses 5 could be aspherical lenses.

The detector further comprises a first element 4 which divides the optical unit into mechanically separated different areas (in this example into 4 areas), each one thereof houses a specific filter 6 and lens 5, therefore the light passing through a determined area of the sample will be detected by a specific partition of the sensor 1.

As shown in FIG. 1 the optical unit and the sensor are arranged perpendicularly to the longitudinal axis (A) corresponding to the plane wherein the reaction area of the liquid sample under examination is positioned.

The arrangement described and visible in FIG. 1 makes then possible to perform m independent measurements (wherein m is the number of areas wherein the sensor is partitioned) for each one of the n areas of the reaction of the sample under examination, equaling to a total of n×m independent determinations. Such result could be obtained even by using m independent sensors (each one with the dedicated optical group thereof), but such configuration has obvious economic and performance disadvantages, as it is preferable that the single sensible areas be as close as possible in order to maximize the overlapping of the 'view cones' and then the usable reaction area.

Preferably the used optical sensor will be then of CMOS type and able to make 'imaging' that is constituted by a series of 'pixel' constituting the minimum sensible unit, the described result of the configuration is to have m separate images, each one thereof will have a 1/m resolution with respect to the total one of the sensor (with respect to the pixels analysed by the unit itself). In the detector according to the invention then preferably sensors will be used equipped with a resolution so that even a number of pixel 1/m is sufficient to do an imaging of the reaction areas.

Still by making reference to the embodiment of FIG. 1 the optical unit comprises even a window 8 faced towards the reaction area wherein the liquid sample under examination is placed, transparent at a defined wavelength. The detector 10 even comprises means 7 for fastening the optical unit, in particular such means 7 will comprise a base element 7 having elements for fastening to the transparent window 8.

A device for performing biochemical analyses is also subject of the present invention comprising a detector according to what herein described, in particular devices for performing analyses of real time PCR.

Figure 2:
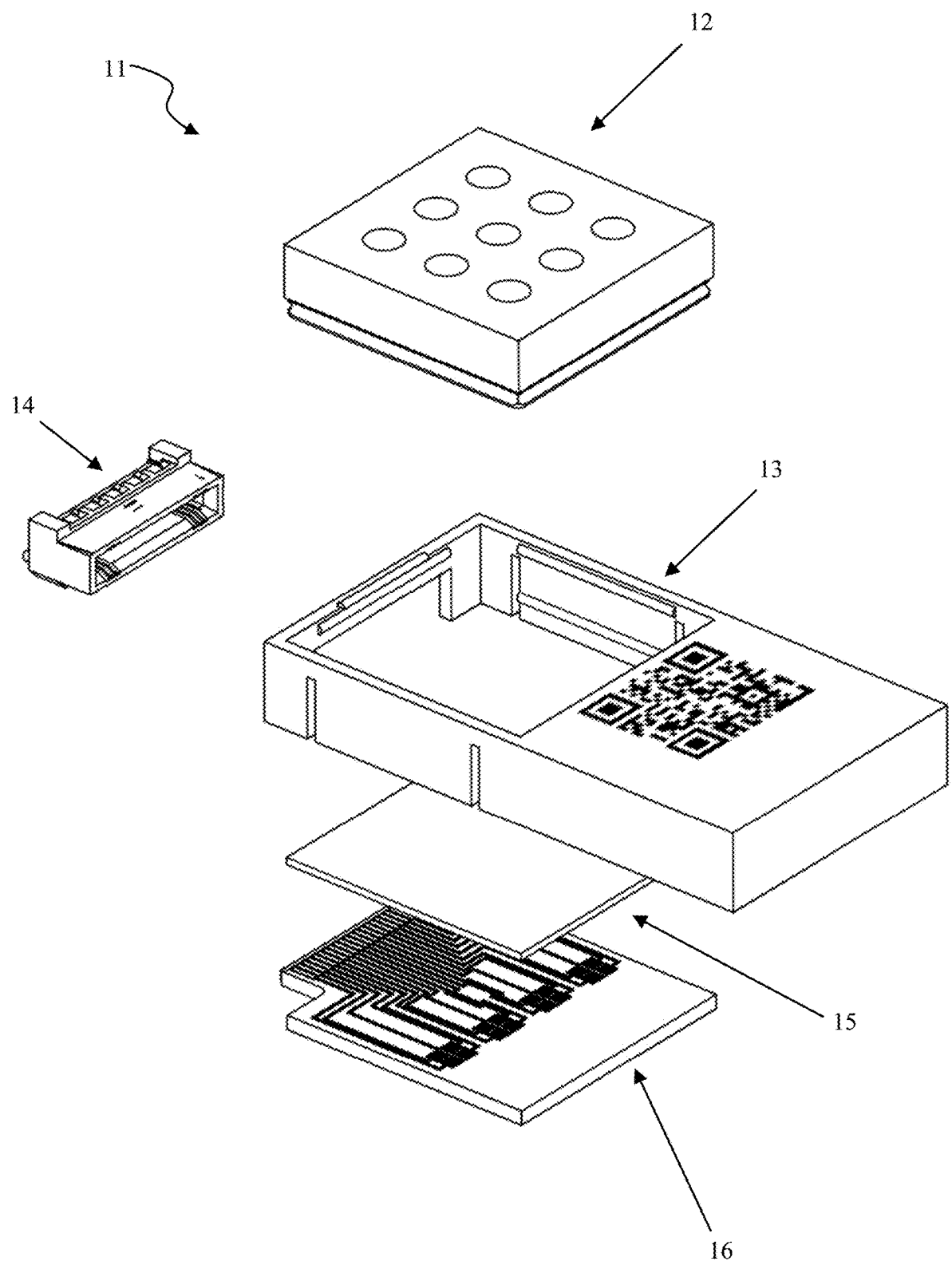
FIG. 2 shows an exploded view of a sample-holding cartridge used in a preferred embodiment of the device according to the present invention.

By making now reference to FIG. 2 a sample-holding cartridge is shown designated as a whole with 11 used in a preferred embodiment of the device according to the present invention.

Such sample-holding cartridge 11 allows the independent and simultaneous detection of optical and electronic events which take place in the liquid sample under examination and it comprises:

a plate 12, or according to other embodiments a set of single smaller plates, preferably made of thermally conductive material, such as for example aluminium;

an optional frame 13 placed around said plate 12 for handling and providing the structures used to seal the plate after charging the reagent;

a cover 15 used for sealing the cartridge, made of a transparent material to allow the passage of optical source to the reaction which takes place in the sample;

an optional electrical interface 14, 16 for electrically connecting the cartridge to the elements existing in the device for electrical measurements and/or impedance. Such elements existing in the device could be the means for electrical measurements and/or impedance known to the person skilled in the art.

More in details the electric interface is constituted by a connector 14 and an electronic board 16 having electrodes connected by means of suitable wire assembly (for example traces made of Cu or other metal lying above or inside the electronic board 16) and which end in the connector 14. Therefore, the reactions in the sample under examination take place in electric contact with a suitable electronic board 16 which is in the device and which through impedance, voltage, amperage measurements performs the wished measurements.

With respect to the cartridges of the state of art, such as for example the plates of the devices to perform Real-Time PCR measurements offering the possibility of performing optical or electronic measurements, there are not cartridge modules allowing to perform independently both types of analyses on the same device. The herein represented possibility of using different axes regarding the cartridge to perform measurements or handling of different nature (in the herein represented example optical measurements according to an axis and electronic measurements according to another axis perpendicular thereto) one can extend to include additional for example mechanical and thermal interactions, wherein the same motion and heat quantity is extracted from the cartridge (the pressure plate and the heating element described subsequently in the specific embodiments).

Examples of using electronic measurements include the electronic detection of hybridization events of surface proteins of determined cells (for example, tumour cells, bacteria) with antibodies immobilized on electrodes placed inside 'small wells' existing in the cartridge. The impedance variation on the electrode given by the cellular mass linked to the same can be detected and it designates the presence in the sample of the cellular species which one wants to detect.

Figure 3:
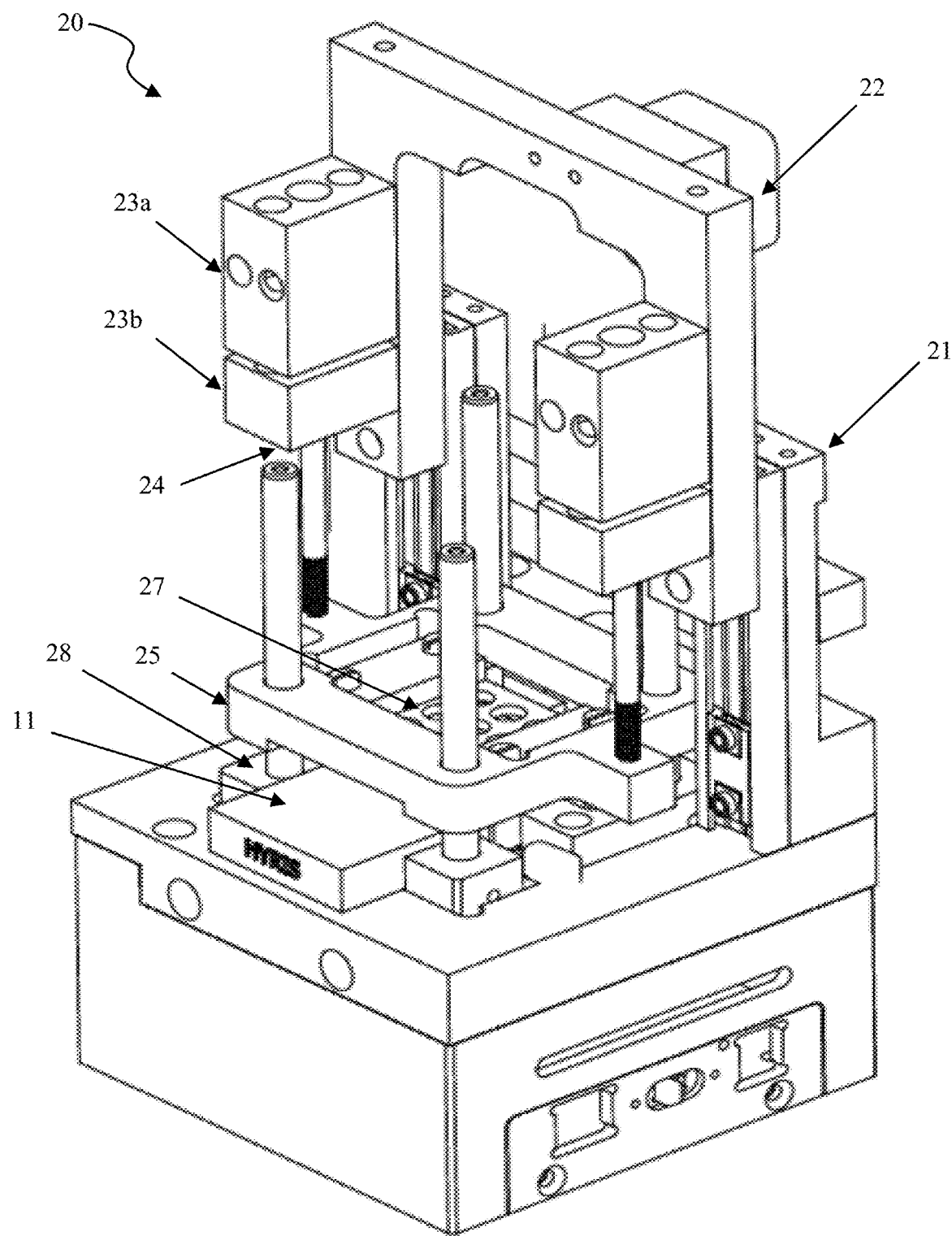
FIG. 3 shows a perspective view of a motion mechanical system in the "open" configuration thereof used in a preferred embodiment of the device according to the present invention.
Figure 4:
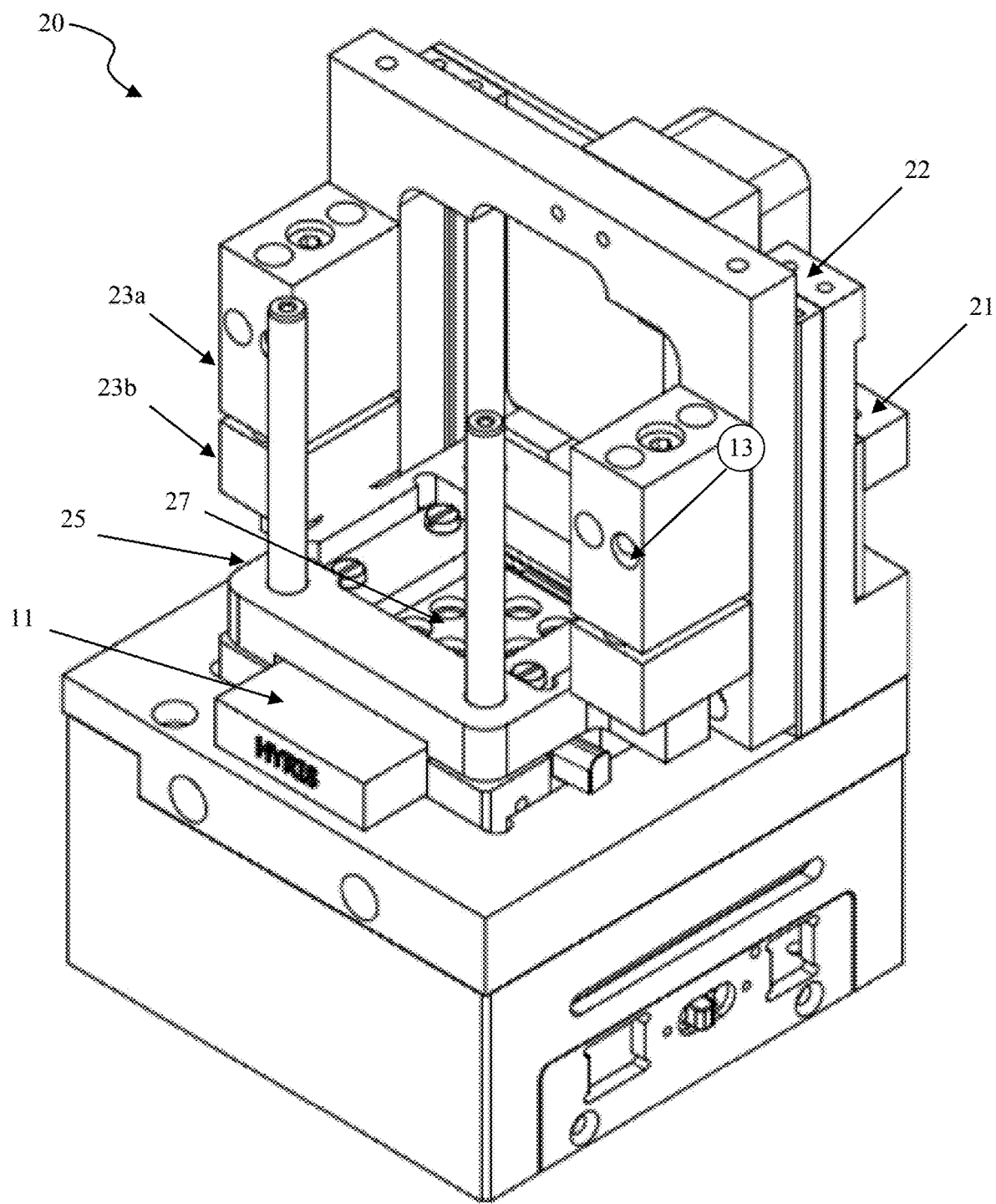
FIG. 4 shows a perspective view of the same motion mechanical system of FIG. 3 in the "closed" configuration thereof.

By making now reference to FIGS. 3 and 4 a motion mechanical systems is shown, designated as whole with 20 respectively in the 'open' configuration thereof, wherein the cartridge is inserted or removed and in the 'closed' configuration thereof, wherein the analysis is performed.

The system 20 has essentially a layout developing longitudinally with respect to the device, therefore the opening and closing mechanism takes place by means of moving vertically the closing lock. This allows inserting into the mechanism a pressure plate 27 which in the closing step exerts a predetermined pressure on the upper face of the cartridge (for example by means of the presence of springs in the motion mechanism).

The arrangement is so that the upper lock can be raised to open the device (that is the analysis instrument) and allow the insertion of the sample holder, whereas by lowering the upper portion the closure of the device is obtained, and to cause the pressure plate 27 to exert onto the sample holder a pressure predetermined for example by the springs or by other equivalent mechanism.

This differentiates from the metallic masks used in the instruments of real time PCR of the state of art, as these have only the purpose of heating the upper portion of the sample holder (in that case a plate) to avoid condensations, but not exerting a significant pressure, as they are simply rested.

The use of this system and in particular of the pressure plate 27, and of a geometry spreading vertically as described, apart from this effect (the pressure plate too is a temperature which can be controlled by means of suitable circuit) has different advantages there among:

improving the thermal exchange with the cartridge housing, when this takes place by thermal conduction with the sample holder (almost all cases);

guaranteeing an optimum electric contact for example among the bump contacts on the lower surface of the sample holder and of the pogo pin lying in the housing;

improving the mechanical sealings when the reaction volumes are closed, for example, by stoppers or other methods subjected to pressure from inside of the reaction volume;

masking spurious lights which could reach the sensor;

transferring kinetic energy to the cartridge itself, for example to break vesicles filled up with reagents in a suitable moment of the analysis reactions, transferring fluids from a region of the cartridge to another one and sealing reaction volumes, in case even by using graduated 'pins' on the face of the pressure plate directed towards the cartridge itself and by segmenting the total motion of the pressure plate in a series of separated passages.

According to the embodiment represented schematically in FIGS. 3 and 4 the mechanical system 20 comprises a first slide frame 21 integral with the device. To this first frame a second mobile frame 22 is connected by means of a slide mechanism (with tracks).

On the mobile frame 22 means (23*a*, 23*b*, 24) are fastened to exert the pressure on the pressure plate (and then on the cartridge) in the 'closed' configuration.

According to the embodiment represented in figure said means for exerting the pressure on the pressure plate comprises first 23*a* and second elements 23*b* spaced apart therebetween by springs. Said second elements 23 engage onto the screws 24 which belong to the pressure plate group. The screws 24 push then downwards the framework 25 and consequently the pressure plate 27 towards the cartridge, which engages in the housing 28.

Figure 5:
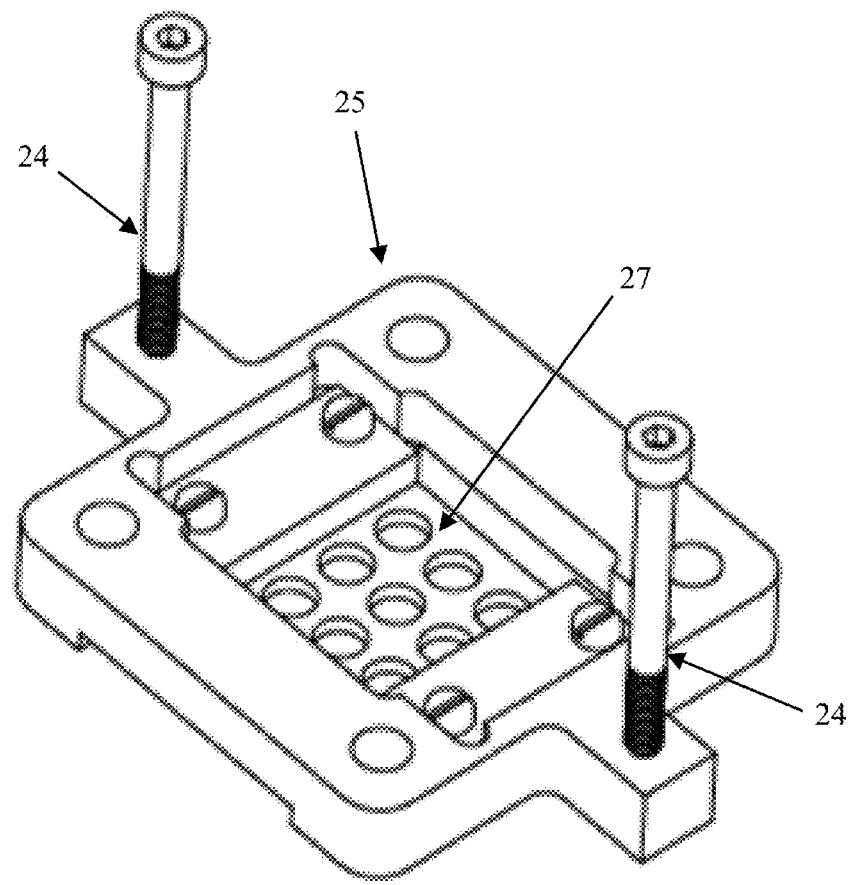
FIG. 5 shows a perspective view of the pressure plate group used in the mechanical system of FIGS. 4 and 5.

FIG. 5 shows in details the pressure plate group. The pressure plate group positioned in the example of FIGS. 3 and 4 in the centre of the system, it has a number of holes equal by position and sizes to the reaction volumes in the immediately underneath sample holder, and rested upon the lower portion in the housing thereof. The pressure plate group comprises a pressure plate 27 integral to the frame thereof (framework) 25, and then to the upper portion of the system. The frame of the pressure plate 25 being fastened mechanically to the pressure plate 27 transmits the motion and the closing pressure to the pressure plate itself. Preferably, the shape of the pressure plate group will be suitable to enter a housing placed in case on the cartridge, wherein the thermally active portion forms a recess with respect to the supporting frame of the cartridge.

Figure 6:
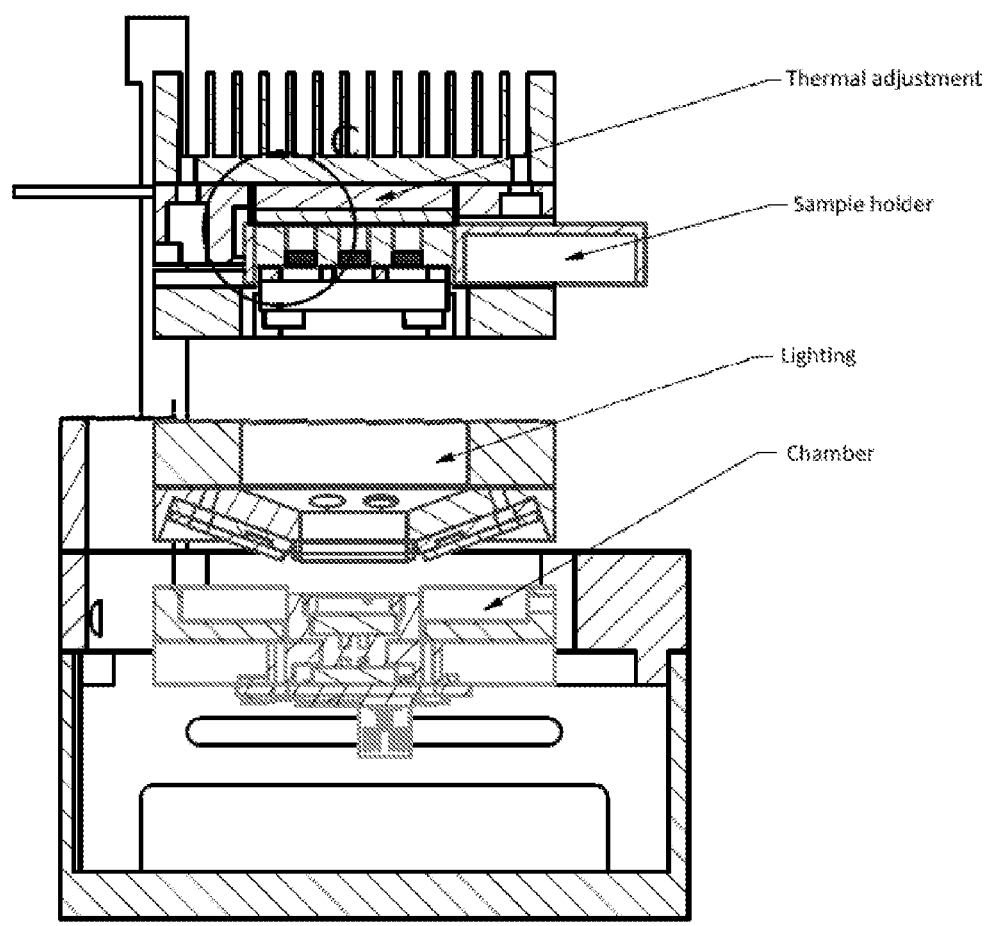
FIG. 6 shows a longitudinal section of the configuration of a preferred embodiment of the device according to the present invention.

The system optionally could comprise a releasing/hooking mechanism, such as for example those available on the market, which once having closed the mechanism keeps it in position and it can be activated to release the mechanism in the opening step. FIG. 6 shows in details the configuration of another embodiment of the device mainly providing the overturning of the arrangement of some portions of the instrument and in particular:

the sample lighting takes place from the bottom upwards (the optical group is then below the sample holder);

the geometry of the optical group remains unchanged, all elements being in relative identical positions with respect to the previously described embodiments;

the heating element, exemplified as aluminium plate 12, instead, is 'above' the sample holder 11 and the heating (and/or cooling) surface contacts the upper surface of the sample holder 11.

As to the 'vertical' mechanical motion, two variants could be provided, the first one wherein the heating element is 'mobile' with respect to the structure and pushes against the sample holder, the second one wherein the sample holder, rested on an adequate mechanism with a function of releasing and graduating the pressure (for example springs), is pushed from the bottom against the heating element.

Figure 7:
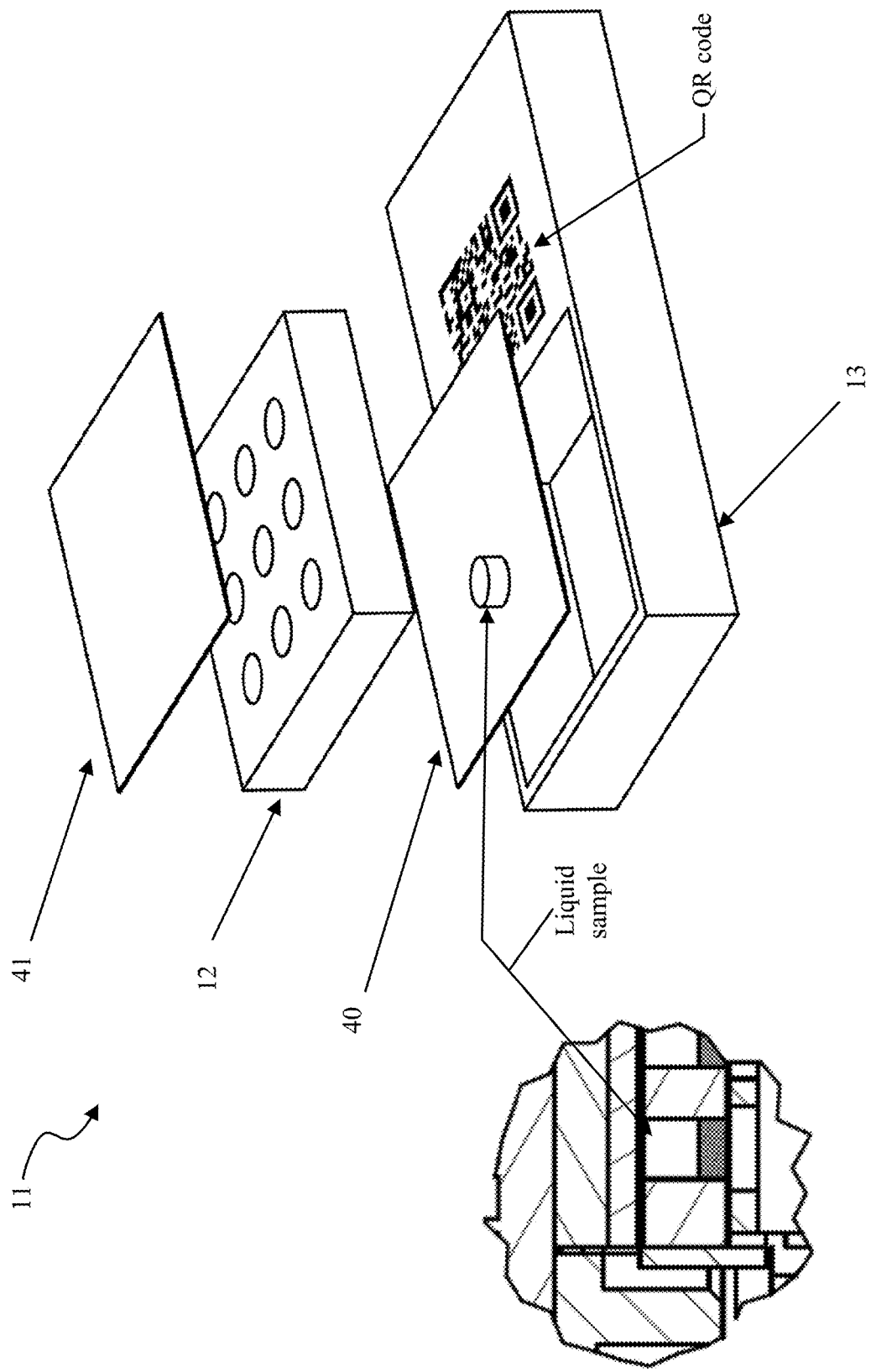
FIG. 7 shows an exploded view of a sample-holding cartridge used in a preferred embodiment of the device according to the present invention.

FIG. 7 describes in details an embodiment of the sample holder 11 which can be used in the device according to the present invention. The sample holder could be entirely made of the same material or, alternatively, of a thermally conductive portion (for example aluminium) and with suitable properties (for example, reflectivity, its own fluorescence), in turn incorporated in the frame 13 allowing the handling and mechanical interfacing thereof. The sample holder could provide through holes crossing it from one side to the other one.

By still referring to FIG. 7 the device could comprise even an optical window 40 positioned on the lower face of the sample holder (for example by gluing, adhering, or mechanical locking). The optical window 40 could be integral with the frame for example by moulding in a single piece. The main feature of the optical window 40 will be that of being transparent at the wavelengths of interest. The device could further comprise even an adequate mechanism for closing the upper face of the sample holder, for example by means of an adhesive and thermo-conductive film 41. Advantageously through this element the heat flows, heating/cooling the sample holder, but not the light (which instead arrives from the bottom).

This configuration has additional advantages shown hereinafter:

a. Typically when the closing of the reaction volumes takes place on the same side of optical reading, this creates criticalities due to the not-perfect compromise between adhesion property and sealing against pressure in the volume heated with the properties of optical transparency.

b. Furthermore if the liquid sample is on the 'bottom' of the reaction volume with respect to the sensor, the film or closing stopper becomes the coldest point in said volume wherein condensate is generated under the form of small drops. This forces to integrate an additional heating mechanism.

c. The reaction volume in the described configuration is in direct contact with the optical window (gravity makes that one rests thereupon), by producing two advantages: on one side the intensity of the signal increases as the volume emitting the signal is not on the 'bottom' of the small well from the sensor point of view, and the closing process with the optical window takes place during production and it is not responsibility of the single operator after having charged the sample. Then the formation of condensate is not possible.

The present invention has been so far described by referring to some preferred embodiments. It is to be meant that other embodiments belonging to the same inventive core may exist, as defined by the protective scope of the here below reported claims.

The invention claimed is:

1. A device for performing biochemical analyses comprising:
    a sample-holding cartridge for containing a liquid sample and having a reaction area for the liquid sample, the sample-holding cartridge comprising:
        one or more plates each comprising a lower surface and an upper surface,
        an optical window positioned on the lower surface of the one or more plates, the optical window being transparent at one or more wavelengths, a frame placed around the one or more plates for handling the sample-holding cartridge after loading the liquid sample;

an adhesive and thermo-conductive film positioned above and contacting the upper surface of the one or more plates;

a cover for sealing the sample-holding cartridge and comprising a transparent material that allows passage of light to the liquid sample; and an electrical interface electrically connected to the sample-holding cartridge to allow for electrical measurements, the electrical interface comprising a connector and an electronic board, the electronic board coupled to the connector and comprising one or more electrodes in electrical contact with the liquid sample and a wire assembly connecting the electrodes to the connector; and a detector for measuring fluorescence in the liquid sample, the detector comprising:

an optical sensor, the optical sensor comprising a single complementary metal oxide semiconductor (CMOS) sensor; and an optical unit mechanically connected to the optical sensor, the optical unit comprising:

a light source for irradiating a reaction area of the liquid sample;

a plurality of optical filters; and a plurality of lenses;

the optical unit being divided into mechanically separated areas, wherein each of the mechanically separated areas houses one of the plurality of optical filters and one of the plurality of lenses, wherein light passing through the reaction area of the liquid sample is detected by one of the mechanically separated areas, and the plurality of optical filters and lenses equals a multiple of two; and the optical sensor being divided into a number m of independent portions corresponding to a number n of the mechanically separated areas of the optical unit, wherein light emitted in the reaction area of the liquid sample is detected by each of the independent portions of the optical sensor, thus performing m independent measurements for the reaction area of the liquid sample.

2. The device of claim 1, wherein the plurality of optical filters comprises different wavelengths.

3. The device of claim 1, where one of more of the plurality of lenses are aspherical lenses.

4. The device of claim 1, wherein the number m is equal to four.

5. The device of claim 1, wherein the optical unit and the optical sensor are arranged perpendicularly to a longitudinal axis corresponding to a plane of the reaction area of the liquid sample.

6. The device of claim 1, wherein the optical sensor and the optical unit are arranged on the same side of the reaction area of the liquid sample.

7. The device of claim 1, wherein the one or more plates are constructed of a thermally conductive material.

8. The device of claim 7, wherein the thermally conductive material is aluminium.

9. The device of claim 1, wherein a resolution of the optical sensor is 1/m.

10. The device of claim 1, the electrical measurements comprising at least impedance, voltage, and amperage.

11. The device of claim 1, wherein the light source is located below the sample-holding cartridge and irradiates the liquid sample in an upwards direction.

12. The device of claim 1, further comprising:

a mechanical handling system for insertion and extraction of the sample-holding cartridge within the device, the mechanical handling system comprising:

a pressure plate group comprising a pressure plate and a frame mechanically fixed to the pressure plate such that movement and a predetermining closing pressure is transmitted to the pressure plate, the pressure plate group being located above the sample-holder cartridge and having a number of holes equal in position and size to each liquid sample reaction volume located on the sample-holder cartridge.

13. The device of claim 12, the mechanical handling system further comprising:

a slide frame and a movable frame, wherein the slide frame is integral with the device and linked to the movable frame via a slide mechanism and the pressure plate is fastened on the movable frame.

14. The device of claim 13, wherein the pressure plate comprises:

first elements and second elements spaced apart therebetween by springs and a plurality of screws, wherein the second elements engage on the screws so as to push downwards the pressure plate.

15. The device of claim 1, wherein the frame includes a QR code.

16. The device of claim 1, wherein the optical window is integrated with the frame as a single piece.

17. The device of claim 1, wherein the adhesive and thermo-conductive film covers the upper surface of the one or more plates.

18. The device of claim 1, wherein the optical window is positioned on the lower surface of the one or more plates by at least one selected from the group consisting of gluing, adhering, or mechanical locking.

19. The device of claim 1, wherein the multiple of two is equal to one of 4, 6, 8, 10, and 20.

20. The device of claim 5, wherein the electrical interface is arranged parallel to a plane of the reaction area of the liquid sample.

* * * * *